United States Patent [19]
Shirasawa et al.

[11] Patent Number: 5,907,399
[45] Date of Patent: May 25, 1999

[54] PARTICLE MEASUREMENT APPARATUS

[75] Inventors: Yoshiaki Shirasawa; Tetsuya Yamamoto, both of Tsukuba, Japan

[73] Assignee: Kowa Company Ltd., Japan

[21] Appl. No.: 08/095,958

[22] Filed: Jul. 22, 1993

[30] Foreign Application Priority Data

Aug. 4, 1992 [JP] Japan .................................. 4-206891

[51] Int. Cl.⁶ .................................................. G01N 15/02
[52] U.S. Cl. ............................ 356/336; 356/338; 356/343
[58] Field of Search .................................. 356/335–343, 356/39; 250/574, 222.2

[56] References Cited

U.S. PATENT DOCUMENTS

| | | | |
|---|---|---|---|
| 4,397,549 | 8/1983 | Morgan | 356/342 |
| 4,492,472 | 1/1985 | Asano et al. | 356/394 |
| 5,015,094 | 5/1991 | Oka et al. | 356/336 |
| 5,059,395 | 10/1991 | Brittenham et al. | 356/335 |
| 5,090,808 | 2/1992 | Ishikawa et al. | 356/336 |
| 5,257,087 | 10/1993 | Furuya | 356/336 |

Primary Examiner—Hoa Q. Pham
Attorney, Agent, or Firm—Adams & Wilks

[57] ABSTRACT

Light receiving elements detect the intensity of light scattered from a sample cuvette containing particles irradiated by a laser beam from a laser source. Signals from the light receiving elements are evaluated to determine the size and number of the particles for its time-series display. In measuring blood corpuscles, the clumps of aggregation can be determined in terms of size and number on a time-series base with high accuracy, thus providing a useful means mechanism for clinically diagnosing various diseases including thrombosis and for determining the effectiveness of remedies.

10 Claims, 5 Drawing Sheets

INVENTIVE APPARATUS

AGGREGATION REACTION WITH 0.3 μm ADP

COMMERCIAL AGGREGOMETER

INVENTIVE APPARATUS — AGGREGATION REACTION WITH 0.7 μg/ml COLLAGEN IN PRESENCE OF 2mMCa$^{2+}$

INVENTIVE APPARATUS — AGGREGATION REACTION WITH 0.7 μg/ml COLLAGEN IN PRESENCE OF Ca$^{2+}$-FREE

COMMERCIAL AGGREGOMETER

Collagen 0.7 μg/ml      3 min

PARTICLE MEASUREMENT APPARATUS

BACKGROUND OF THE INVENTION

1. Field of the Invention

The present invention relates to a particle measurement apparatus, and more particularly to an apparatus for measuring the aggregation capability or aggregation rate of platelets and other blood corpuscles.

2. Description of the Prior Art

Because of the precise picture it provides of the aggregation reaction, knowledge of the size and numbers of clumps (aggregates) of platelets and other such agglutinable blood corpuscles is essential for diagnosing various diseases. For this purpose, there are known blood platelet aggregability measurement apparatuses that measure such aggregates of particles. In a conventional apparatus for measuring platelet aggregability, for example, a sample cuvette containing a platelet solution is irradiated by a visible ray, and light transmitted and scattered from a wide area that includes many aggregates is converted to electrical signals by a light receiving element, and the intensity thereof is used to determine platelet aggregation.

Measuring as it does the intensity of light transmitted and scattered from a wide area that includes large numbers of aggregates, a drawback of the prior art is that although the size and the number of aggregates are faithful indicators of quantitative changes in the aggregation reaction, both quantities cannot be measured on a time-series basis. Moreover, because in the early stages of the aggregation reaction the intensity of scattered light from large numbers of non-aggregated blood platelets is much stronger than the intensity of scattered light from the small number of aggregates, are prevented changes in aggregation, from accurately being ascertained. In practice, with conventional measurement apparatus, such changes cannot be established even when there are aggregates of 30 to 40 percent of the platelets.

SUMMARY OF THE INVENTION

An object of the present invention is to provide a particle measurement apparatus that is capable of time-series measurement of the size and number of platelet aggregates.

An apparatus in accordance with the present invention is adapted to measure properties of particles by measuring the intensity of light scattered from a sample cuvette containing the particles and comprises a laser light source for producing a laser beam, means for collimating the laser beam from the laser light source to project it at the sample cuvette, light receiving means for receiving light scattered from the sample cuvette, measuring means for evaluating signals from the light receiving means and measuring the diameter and number of particles, and means for displaying particle size and number measured on a time-series basis.

With this arrangement, the size and quantity of particles can be measured on a time-series basis, making it possible to determine multiple properties of the particles.

In a preferred embodiment, the measuring means consists of a plurality of comparison means that have upper and lower threshold values corresponding to particle diameter and respective comparison means discriminate particle diameters by comparing signals from the light receiving element with each threshold value, and counter that count output signals from each of the comparison means, wherein said apparatus performs time-series measurement of particle diameters and quantities number discriminated into classes corresponding to the number of comparison means.

It is also possible to use an arrangement whereby the light receiving element receives scattered light from substantially one of the target particles, thereby enabling the precision of the measurements to be improved.

The apparatus could also be arranged so that it is provided with multiple light receiving elements and simultaneously measures the scattered light received by each element, in which case the output from pairs of light receiving elements could be subtracted to increase the effective signal ratio, thereby improving the signal to noise (S/N) ratio during measurement.

Preferably, this particle measurement apparatus is an apparatus for measuring blood platelet aggregability. In such a case, the particles would be clumps of agglutinable blood corpuscles, such as platelets, and it would be the aggregability or aggregation rate of such corpuscles that would be measured. With the apparatus arranged thus to measure platelet aggregability, the size and numbers of aggregates of platelets or other corpuscles in the aggregation reaction can be measured in terms of a time-series, thereby providing a more faithful observation of the aggregation reaction. With such a measurement it also becomes possible to measure small aggregates in a weak aggregation reaction.

DETAILED DESCRIPTION OF THE PREFERRED EMBODIMENTS

Figure 1:
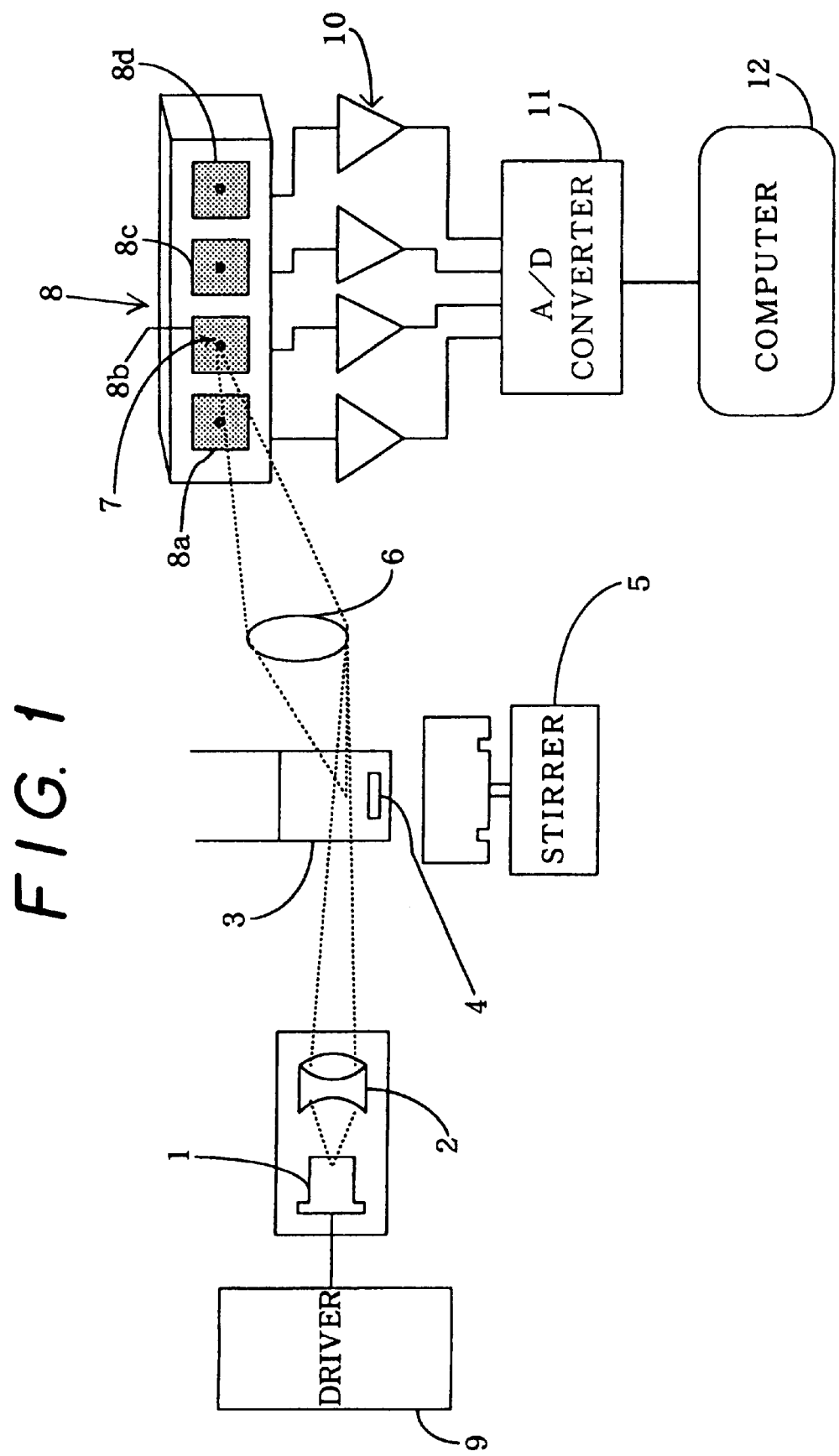
FIG. 1 illustrates the general arrangement of a particle measurement apparatus according to this invention.

Details of the present invention will now be described with reference to the embodiment illustrated in the drawings. In this embodiment the description relates to an example of the particle measurement apparatus configured to measure platelet aggregability.

This type of platelet aggregation measurement apparatus is illustrated in FIG. 1. With reference to FIG. 1, for measuring the intensity of scattered light, a semiconductor laser light source 1 (40 mW) is driven by a drive circuit 9 to generate a beam of laser light. The laser beam collimated by converging lens 2 impinges on a glass sample cuvette 3 which contains a suspension of blood platelets or other such blood corpuscles. The suspension of blood corpuscles in the sample cuvette 3 is maintained at a constant temperature of 37° C. and stirred at 1000 rpm by means of a stirring bar 4 and magnetic stirrer 5.

Scattered light from the suspension of blood corpuscles passes via light receiving lens 6 to a plurality of photodiodes 8 (8a to 8d) and is thereby measured as an electrical signal. Disposed in front of each of the photodiodes is a (10-by-100 micrometer) pinhole 7 that receives scattered light from an observation region that statistically permits measurement of only one clump. The output of the photodiodes 8 undergoes current-voltage conversion and amplification by an amplifier 10, followed by analog-digital conversion by an A/D converter 11, and is then input to a computer 12.

In the computer 12, the signal level is discriminated by a plurality of comparators corresponding to the clump particle diameter, and the signals output by the comparators are counted to thereby measure the number of clumps there are of each prescribed particle diameter. An erroneous clump particle diameter count caused, for example, by part of a clump crossing an edge portion of a pinhole 7 can be corrected by personal computer measurement software, using statistical probability theory and standard particle measurements.

Figure 2:
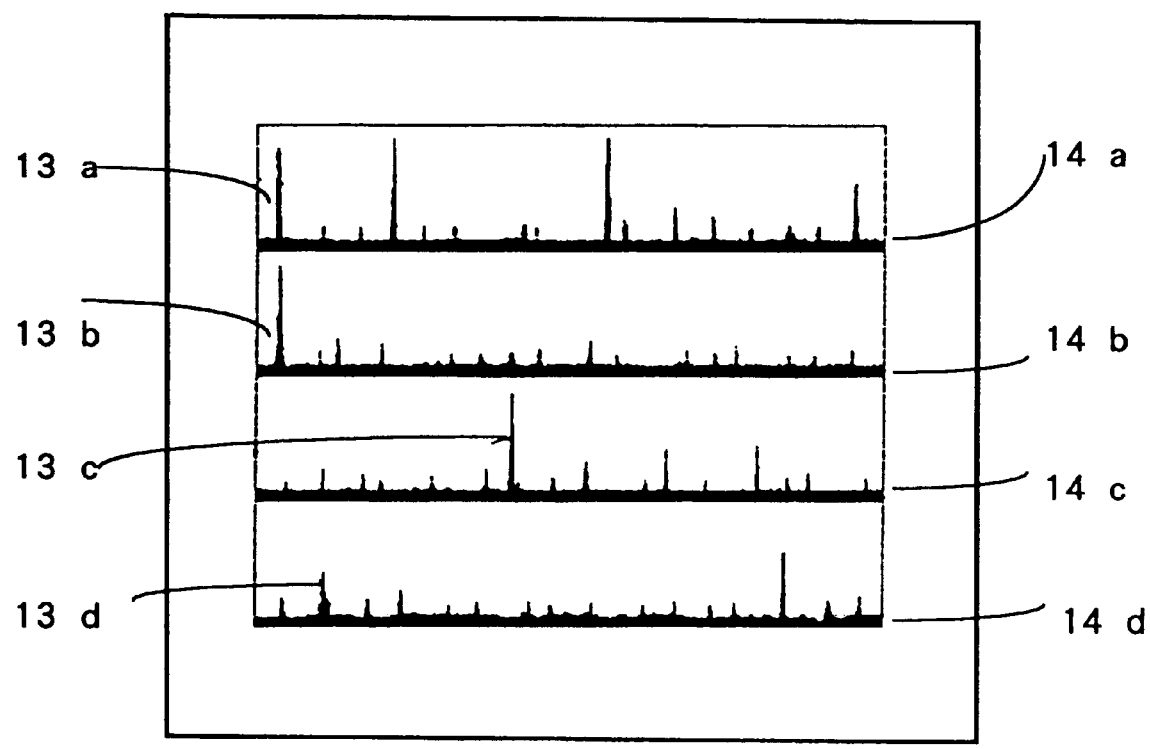
FIG. 2 is a waveform of a scattered light intensity signal obtained from light receiving elements of the apparatus of FIG. 1.

FIG. 2 shows changes in the intensity signal of light scattered during the aggregation of platelets, measured by one of the photodiodes 8a to 8d. The scattered light from the aggregate is measured as peak signals 13a to 13d that are correlated with aggregate size, and scattered light from individual, non-aggregated corpuscles is measured as background signals 14a to 14d.

Figure 3:
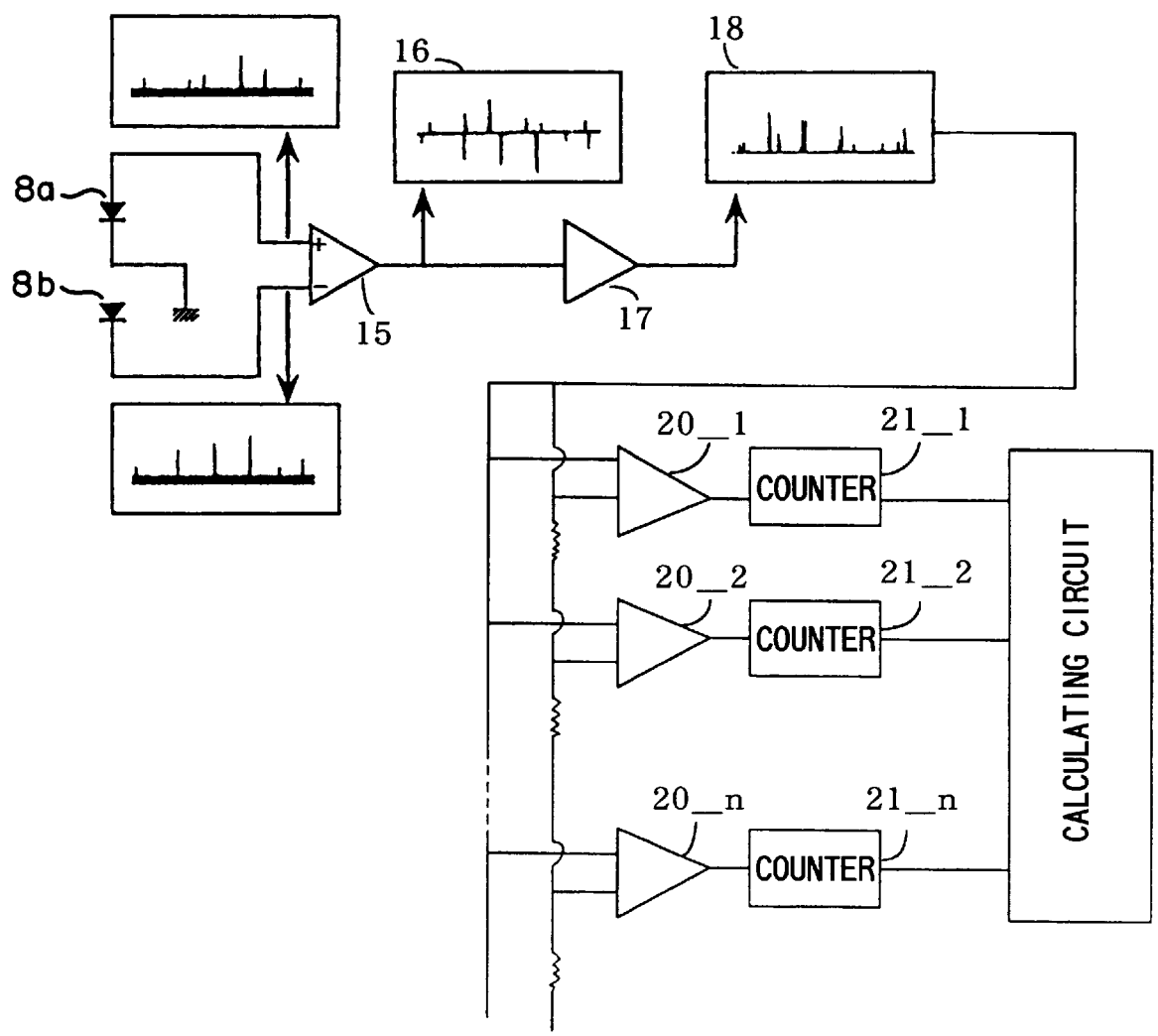
FIG. 3 is a schematic of the signal processing circuit.

To eliminate the effect of these background signals, as shown in FIG. 3, the outputs from two photodiodes 8a and 8b are each input to an operational amplifier 15 and subjected to subtraction. In this way, background signals produced by scattered light from non-aggregated corpuscles are canceled out, and only scattered light intensity values from clumps are measured, as indicated by 16. Signals from which background has thus been eliminated are then input to an absolute value circuit 17, which outputs background-free peak signals, as shown by 18.

The signal output of the absolute value circuit 17 is input to window comparators 20_1, 20_2 . . . 20_n where the level thereof is discriminated. Each comparator compares the signal with a level corresponding to a clump particle diameter, so the output of each comparator is a signal corresponding to a clump particle diameter. These signals are counted by respective counters 21_1, 21_2 . . . 21_n to count the number of clumps of that particle diameter. This count data is then input to a calculating circuit 22, which computes the data representing the clump particle diameter and quantity, as described below. The functions of the comparators, counters and calculating circuit are implemented in the computer 12.

While FIG. 3 was used to describe the processing of the signals output by photodiodes 8a and 8b, the processing is the same for the other photodiodes 8c and 8d. Multiple sets of light receiving element pairs are used to raise the clump count probability.

Figure 4A:
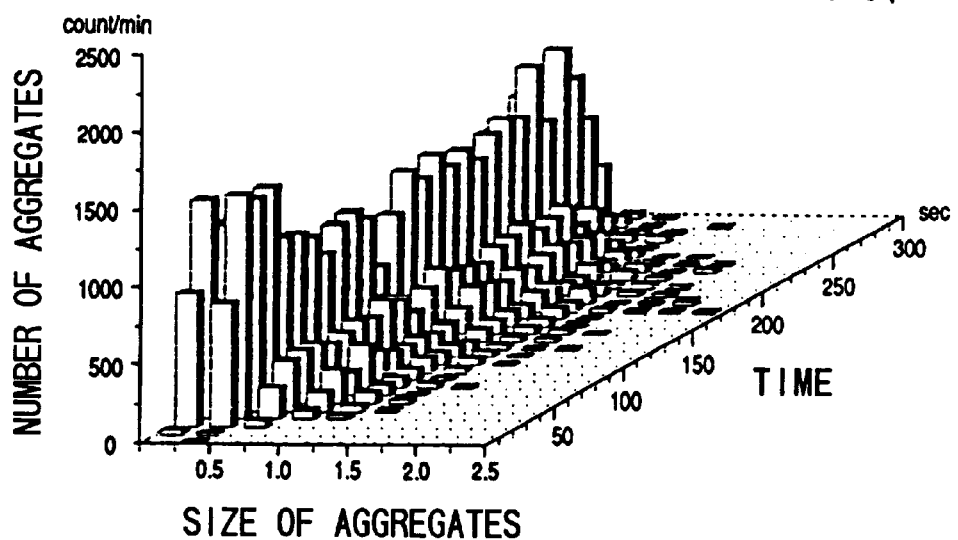
FIG. 4A shows aggregation reaction data measured by the apparatus according to this invention.
Figure 4B:
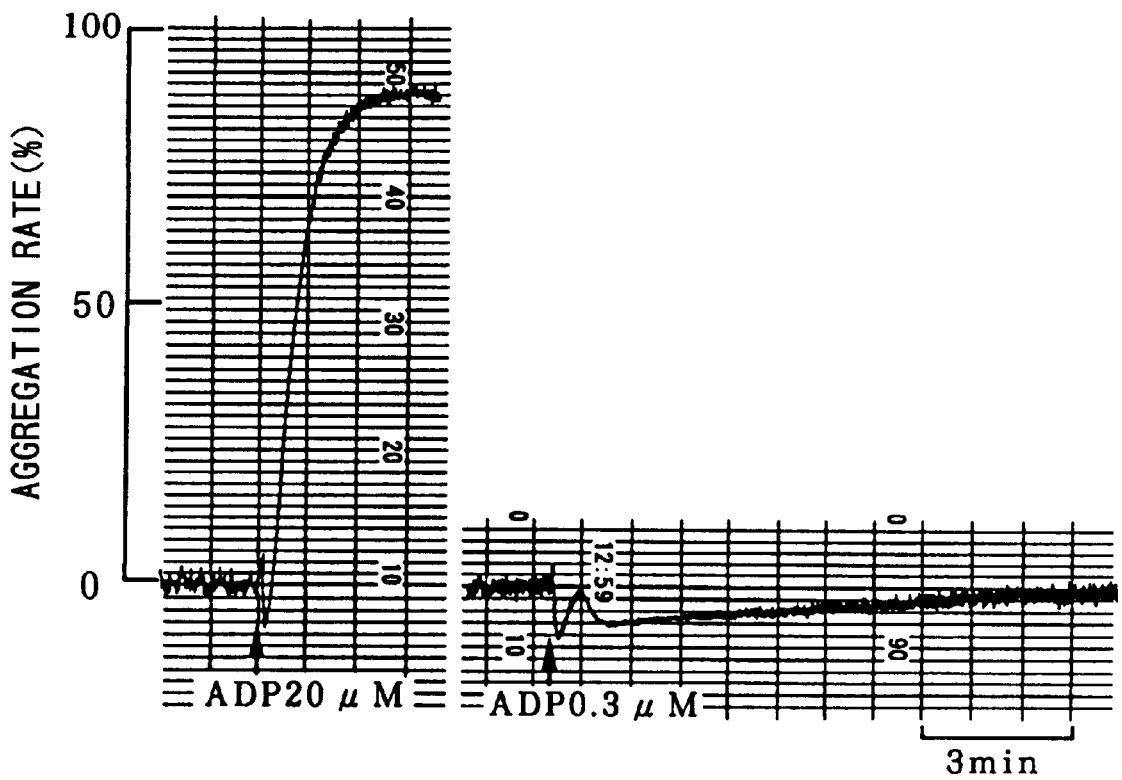
FIG. 4B shows data measured by a conventional apparatus.

FIGS. 4 and 5 illustrate blood platelet aggregation, as measured by the apparatus of the present invention and by an apparatus for measuring blood platelet aggregability according to the prior art. With respect to measured results of blood platelet aggregation reactions induced using ADP (adenosine diphosphate) as the agglutinin, FIG. 4A shows data obtained with a measurement apparatus according to this invention, and FIG. 4B shows data obtained using a conventional apparatus for measuring blood platelet aggregability (a commercial aggregometer).

As shown by FIG. 4B, the conventional measurement apparatus does not measure aggregation reactions induced by an ADP concentration of 0.3 micromoles/liter or less. In contrast, as shown by FIG. 4A, with the measurement apparatus according to this invention, with the comparators 20_1, 20_2 . . . 20_n particle diameters are discriminated in terms of aggregate particle size, and counts of these particle sizes are displayed along a time line as the number of aggregates. Also, the formation of many aggregates were observed when ADP in a concentration of 0.3 micromoles/liter was added. With this measurement apparatus, it is also possible to measure aggregation reactions produced by ADP at the low concentration of 0.03 micromoles/liter. This means that an apparatus embodying the present invention is capable of measuring aggregation reactions with 30 times the sensitivity of a conventional apparatus. Moreover, with the inventive apparatus it is possible to measure the size distribution and numbers of aggregates along a time baseline, and to observe how over time the aggregation reaction is accompanied by the formation of large aggregates from smaller aggregates.

Figure 5A:
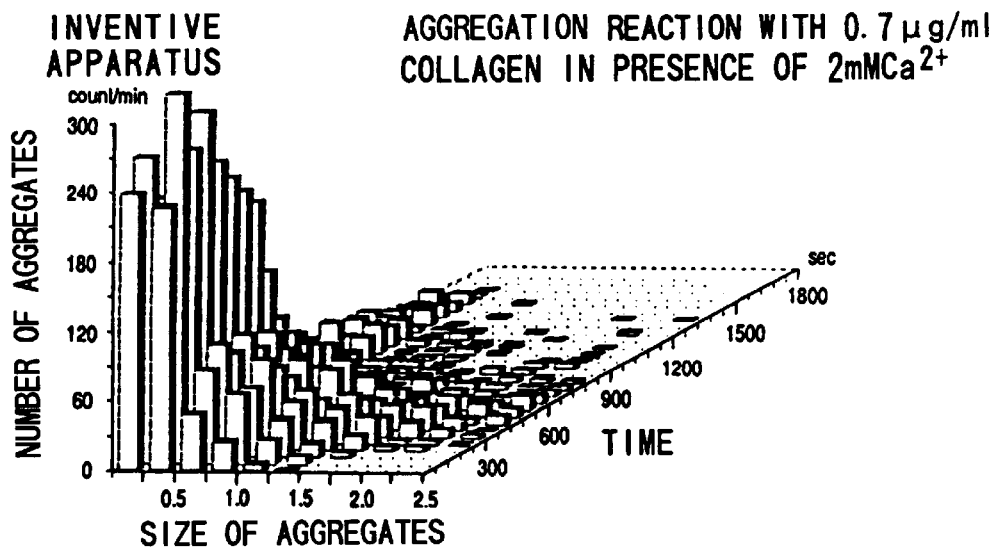
FIGS. 5A and 5B show aggregation reaction data measured by the apparatus of this invention.
Figure 5B:
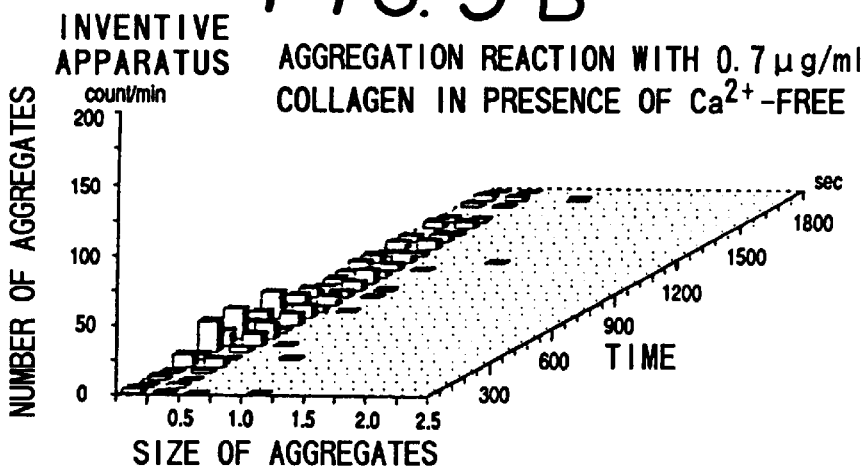
Figure 5C:
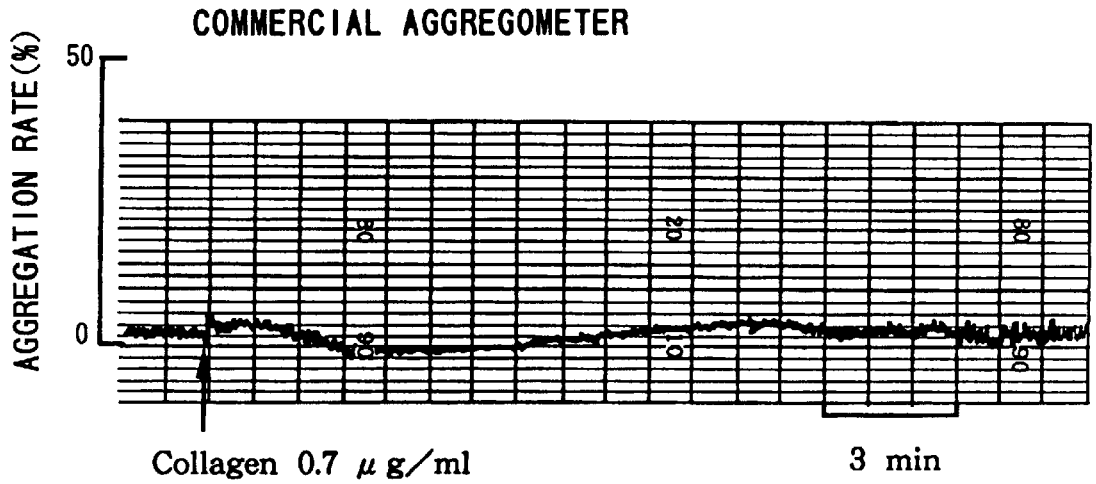
FIG. 5C shows data measured by a conventional apparatus.

FIG. 5 also illustrates blood platelet aggregation measurement by the apparatus of this invention and by a conventional apparatus for measuring blood platelet aggregability. With respect to measured results of blood platelet aggregation reactions induced using a collagen agglutinin, FIGS. 5A and 5B show data obtained with a measurement apparatus according to this invention, and FIG. 5C shows data obtained using a conventional apparatus for measuring blood platelet aggregability (aggregometer). As shown by FIG. 5C, an aggregation reaction induced by adding 0.7 micrograms/ml collagen could not be observed with the conventional measurement apparatus. As shown by FIG. 5A, however, the formation of numerous aggregates resulting from the addition of 0.7 micrograms/ml collagen was observed with the measurement apparatus according to this invention. Moreover, as shown by FIG. 5B, also observed was the clear suppression of aggregation induced by the addition of 0.7 micrograms/ml collagen in a calcium-ion-free solution containing EGTA (ethylenglycol tetraacetic acid) to suppress platelet aggregation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring properties of particles by measuring the intensity of light scattered from a sample cuvette containing the particles, comprising:

a laser light source for producing a laser beam;

means for collimating the laser beam from the laser light source to project it at the sample cuvette;

light receiving means comprising a plurality of light receiving elements each of which receives light scattered from the sample cuvette and produces an output signal whereby the plurality of light receiving elements effect simultaneous measurement of the received light;

means disposed between the sample cuvette and the light receiving means for passing light scattered from selected particle sizes;

measuring means for evaluating the output signals from the light receiving means and measuring the diameter and number of particles, the measuring means comprising a plurality of comparison means each having upper and lower threshold values corresponding to particle diameter and each operative to discriminate particle diameters by comparing the output signals from the light receiving means with each threshold value, and counters connected to count signals from each of the comparison means, wherein particle diameters and numbers discriminated into class corresponding to the number of comparison means are determined on a time-series basis; and means for displaying particle size and quantity on a time-series basis.

2. An apparatus according to claim 1, in which the light receiving means are arranged to receive scattered light from substantially one particle.

3. An apparatus according to claim 1, in which outputs from pairs of light receiving elements are subtracted to increase the effective signal ratio.

4. An apparatus according to 1, in which the particles are clumps of agglutinable blood corpuscles such as blood platelets, and blood corpuscle aggregability or aggregation rate is measured.

5. An apparatus for measuring the aggregability or aggregation rate of clumps of agglutinable blood corpuscles by measuring the intensity of light scattered. from a sample cuvette containing aggregated blood, comprising:

a laser light source for producing a laser beam;

means for collimating the laser beam from the laser light source to project it at the sample cuvette;

light receiving means comprising a plurality of light receiving elements each of which receives light scattered from the sample cuvette and produces an output signal whereby the Plurality of light receiving elements effect simultaneous measurement of the received light;

means disposed between the sample cuvette and the light receiving means for passing light scattered from selected particle sizes;

measuring means for evaluating the output signals from the light receiving means and measuring the diameter and number of particles, the measuring means comprising a plurality of comparison means each having upper and lower threshold values corresponding to particle diameter and each operative to discriminate particle diameters by comparing the output signals from the light receiving means with each threshold value, and counters connected to count signals from each of the comparison means, wherein the particle diameters and numbers discriminated into class corresponding to the number of comparison means are determined on a time-series basis; and means for displaying particle size and quantity on a time-series basis.

6. An apparatus according to claim 5; wherein the light receiving means is arranged to receive scattered light from substantially one particle.

7. An apparatus according to claim 5; wherein outputs from pairs of light receiving elements are subtracted to increase the effective signal ratio.

8. An apparatus for measuring the aggregability or aggregation rate of clumps of agglutinable blood corpuscles by measuring the intensity of light scattered from a sample cuvette containing aggregated blood, comprising:

a laser light source for producing a laser beam;

means for collimating the laser beam from the laser light source to project it at the sample cuvette;

light receiving means for receiving light scattered from the sample cuvette, wherein the light receiving means comprises a plurality of light receiving elements each of which receives the scattered light and produces an output signal whereby the plurality of light receiving elements effect simultaneous measurement of the received light;

means disposed between the sample cuvette and the light receiving means for passing light scattered from selected particle sizes;

measuring means for evaluating the output signals from the light receiving means and measuring the diameter and number of particles, the measuring means comprising a plurality of comparison means having upper and lower threshold values corresponding to particle diameter and each operative to discriminate particle diameters by comparing the output signals from the light receiving means with each threshold value, and counters connected to count signals from each of the comparison means, wherein the particle diameters and quantities discriminated into class corresponding to the numbers of comparison means are determined on a time-series basis; and means for displaying particle size and quantity on a time-series basis.

9. An apparatus according to claim 8; wherein the light receiving means are arranged to receive scattered light from substantially one particle.

10. An apparatus according to claim 8; wherein outputs from pairs of light receiving elements are subtracted to increase the effective signal ratio.

* * * * *